United States Patent [19]

Bonati et al.

[11] 4,117,133

[45] Sep. 26, 1978

[54] VASODILATING CUANZINE HYDRAZIDES

[75] Inventors: Attilio Bonati; Bruno Gabetta, both of Milan, Italy

[73] Assignee: Inverni Della Beffa S.p.A., Milan, Italy

[21] Appl. No.: 734,173

[22] Filed: Oct. 20, 1976

[30] Foreign Application Priority Data

Oct. 28, 1975 [GB] United Kingdom ............... 44441/75

[51] Int. Cl.$^2$ ................. C07D 519/04; A61K 31/445
[52] U.S. Cl. ............................. 424/256; 260/293.53; 260/293.55; 542/417
[58] Field of Search ............... 260/293.55, 293.53, 260/240 G; 424/256; 542/417

[56] References Cited

U.S. PATENT DOCUMENTS

| 3,830,823 | 8/1974 | Castaigne | 260/293.53 |
|---|---|---|---|
| 3,937,709 | 2/1976 | Sevenet et al. | 260/293.53 |
| 3,950,345 | 4/1976 | Najer et al. | 260/293.53 |
| 3,966,745 | 6/1976 | Giudicelli et al. | 260/293.53 |
| 4,029,659 | 6/1977 | Hannart | 260/293.53 |

FOREIGN PATENT DOCUMENTS 279,060 2/1970 Austria ................................. 260/293.53

OTHER PUBLICATIONS

Bombardelli, E. et al., Tetrahedron, 30, 4141–4146 (1974).
*Organic Reactions,* Adams, R., Ed., vol. 1, John Wiley and Sons, Inc., New York, 1942, pp. 114–117.
*Chemical Abstracts,* vol. 81, 166291t (1974) [Gabetta, B. et al., Fitoterapia 1974, 45(1), 32–36].
*Chemical Abstracts,* 84:150826x (1976) [Belgian Patent 826,668, 6/30/75].
*Chemical Abstracts,* 79:321602 (1973) [German Offen. 2,250,449, 5/3/73].

*Primary Examiner*—Henry R. Jiles
*Assistant Examiner*—Richard A. Schwartz
*Attorney, Agent, or Firm*—Browdy and Neimark

[57] ABSTRACT

Derivatives of the alkaloid cuanzine are described which have valuable pharmacological properties in the cardiovascular field. Also described are processes for producing the derivatives and pharmaceutical compositions containing them.

11 Claims, No Drawings

VASODILATING CUANZINE HYDRAZIDES

This invention relates to novel derivatives of the alkaloid cuanzine, to processes for their preparation and to pharmaceutical compositions containing the novel derivatives.

Cuanzine is a hexacyclic indole alkaloid which can be isolated from the bark of the roots of the plant *Voacanga chalotiana*. Examination of its chemical and spectroscopic properties has enabled the absolute configuration represented by the structural formula I to be assigned to cuanzine, which thus belongs to the class of alkaloids having the eburnane skeleton.

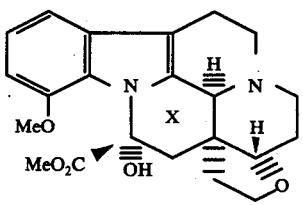

I

Cuanzine and its pharmaceutically acceptable salts possess valuable pharmaceutical properties, particularly anti-arhythmic, vasodilatory and hypotensive properties and are described and claimed in our copending U.K. Patent Application No. 50881/73 (British Pat. No. 1,478,300).

We have now found that by making certain structural modifications at $C_{16}$ and/or $C_{21}$ of the cuanzine molecule, derivatives may be obtained which have particularly valuable pharmaceutical properties in the cardiovascular field, especially as vasodilators and hypotensive agents.

In particular, compounds having more pronounced haemodynamic activities than cuanzine itself may be prepared by making such modifications. Particularly preferred are compounds in which the configuration at C-21 is inverted, compounds in which the carboxymethyl group at C-17 is converted to different functional groups, compounds containing a double bond between C-16 and C-17 and compounds in which ring X (see formula I above) has been opened by reaction with a hydrazine, but in which the cyclic structure of the remaining five rings is maintained.

Thus according to the present invention, there are provided compounds having the general formulae.

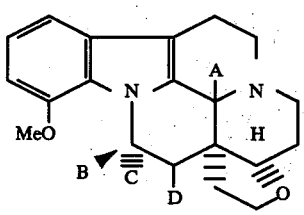

II

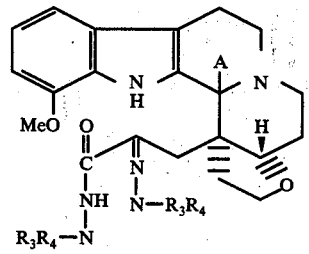

III wherein
A represents a hydrogen atom in the α- or the β-configuration;
B represents an esterified carboxyl group, preferably a group of the formula $-CO_2CH_2CH_2NR_1R_2$ where $R_1$ and $R_2$, which may be the same or different, each represents an alkyl group;
C either represents a hydroxyl group, in which case D represents a hydrogen atom, or C and D together represent an additional bond linking the carbon atoms to which they are attached,
with the proviso that where A is α-hydrogen, C is a hydroxyl group and D is a hydrogen atom, B is other than $-CO_2CH_3$; and $R_3$ and $R_4$, which may be the same or different, each represents a hydrogen atom or an alkyl group.

There are also provided hydrazones obtainable by reacting compounds of general formula III in which the moieties $R_3$ and $R_4$ attached to at least one of the linked pairs of nitrogen atoms are both hydrogen, with ketones or aldehydes. The novel hydrazones are believed to have general formula

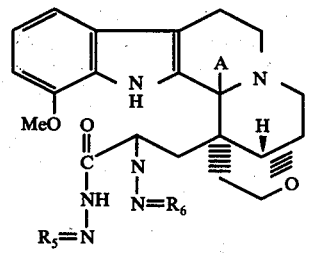

IV wherein
A is defined above and
$R_5$ and $R_6$ are different and each represents two hydrogen atoms or a $=CR_7R_8$ group where $R_7$ and $R_8$, which may be the same or different, each represents an alkyl group or an aryl group or a hydrogen atom.

Examples of representative classes of compounds of general formula II are those having the formulae

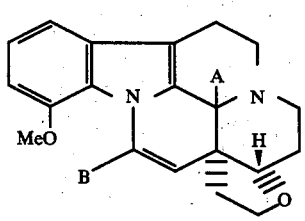

IIA

-continued

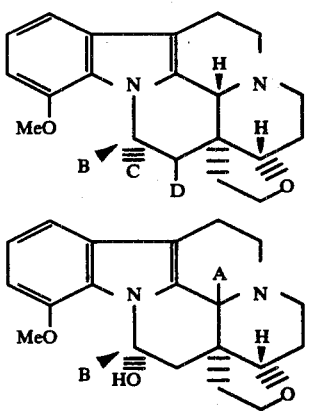
IIB

IIC

The invention also includes the pharmaceutically acceptable salts of the compounds of general formulae II, III and IV. Such salts are those formed with acids yielding pharmacologically acceptable anions including mineral acids such as hydrochloric acid and organic acids such as tartaric acid.

The esterified carboxyl groups represented by B preferably contain 2 to 12 carbon atoms most preferably 2 to 8 carbon atoms and the alkyl groups represented by $R_1$, $R_2$, $R_3$, $R_4$, $R_7$ and $R_8$ preferably contain from 1 to 9 carbon atoms. The aryl groups represented by $C_7$ and $C_8$ preferably contain from 6 to 12 carbon atoms and include aralkyl and alkaryl groups. Specific examples include phenyl, benzyl and tolyl.

The compounds of general formula II may be prepared by subjecting cuanzine (or another derivative of cuanzine of general formula II) to one or more of the following procedures which each constitute further aspects of the present invention:

(i) converting cuanzine or an ester derivative thereof (each being in free form or in the form of a salt) to 21-epicuanzine or a derivative thereof by partial oxidation to form 21,4-dehydrocuanzine of formula V (or a derivative thereof)

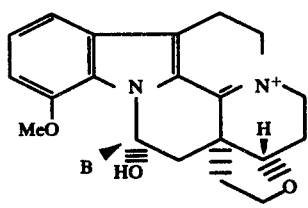
V for example with potassium dichromate or mercuric acetate, followed by reduction to form a compound of formula VI, for example by reaction with a metal and an acid or by hydrogenation in the presence of a catalyst;

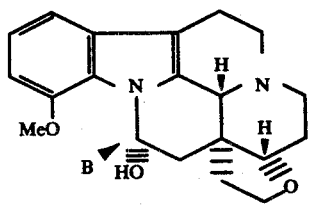
VI (ii) converting cuanzine or an ester derivative thereof (each being in free form or in the form of a salt) to a compound of formula VII by heating in the presence of an aqueous acid;

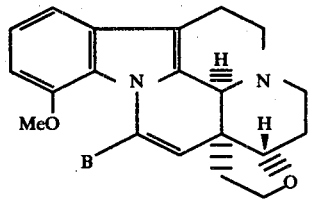
VII (iii) converting cuanzine or epicuanzine or apocuanzine (each being in free form or in the form of a salt) into a compound of formula II having a desired esterified carboxyl group as group B (a) by transesterification with an alcohol, preferably an alcohol having the formula $HOCH_2CH_2NR_1R_2$, where $R_1$ and $R_2$ are as defined above, preferably, in the presence of a nonpolar solvent, or (b) by hydrolysis so as to convert the carboxymethyl group to a carboxyl group, followed by re-esterification, for example by nucleophilic reaction with a compound of formula $XCH_2CH_2NR_1R_2$, where $R_1$ and $R_2$ are as defined above and X is a halogen.

Cuanzine derivatives in which ring X has been opened by reaction with a hydrazine e.g. the compounds of general formula III, may be prepared by reacting cuanzine or a compound of formula II in which C and D are respectively a hydroxyl group and a hydrogen atom (each being in free form or in the form of a salt) with hydrazine or a hydrazine derivative of formula $H_2N-NR_3R_4$, where $R_3$ and $R_4$ are as defined above, in a polar solvent, for example ethanol.

The compounds of general formula IV may be obtained by reacting the above-mentioned derivatives in which ring X has been opened by reaction with a hydrazine, e.g. compounds of formula III (in which $R_3$ and $R_4$ represent hydrogen atoms) with ketones or aldehydes of formula $O=CR_7R_8$, where $R_7$ and $R_8$ are as defined above. The solvent can be either the ketone or the aldehyde itself or a polar solvent, for example, ethanol.

The compounds of general formula II, III and IV may be converted to a pharmaceutically acceptable acid addition salt by treatment with a mineral or organic acid yielding pharmaceutically acceptable anions.

As mentioned above, the compounds of formula II, III and IV are useful as vasodilators and hypotensive agents and thus in accordance with a further aspect of the invention there are provided pharmaceutical compositions comprising a compound of formula II, III and IV or a pharmaceutically acceptable salt thereof and a pharmaceutically acceptable excipient.

Since conversion of the compounds of formula II, III and IV into salts heightens their solubility in water, the use of the salts is preferred where water-solubility is of importance, as in compositions for parenteral administration.

In formulating compositions according to the invention, a wide range of excipients may be used, the nature of which will depend, of course, on the intended mode of application of the composition. Examples include preservatives and buffering, thickening, suspending, stabilizing, wetting, emulsifying, coloring and flavoring agents and in particular carboxy vinyl polymers, propylene glycol, ethyl alcohol, water, cetyl alcohol, saturated vegetable triglycerides, fatty acid esters of propylene glycol, triethanolamine, glycerol, starch, lactose, magnesium stearate, sorbitol, bentonite, carboxymethyl cellulose, lauryl sulphate, dicalcium phosphate, powdered silica, citric acid etc. More than one diluent or carrier is advantageously used.

In formulating compositions for parenteral administration, the excipients should be sterile and pyrogen-free.

The invention will now be described in more detail in the following examples. To clarify the nomenclature used to describe the compounds produced, it will be noted that the compound

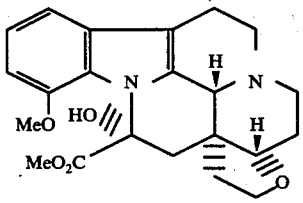

VIII is referred to as 21-epicuanzine, the compound

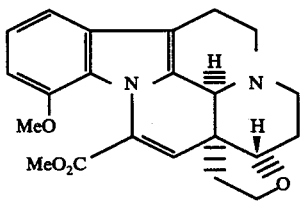

IX is referred to as apocuanzine and the compound

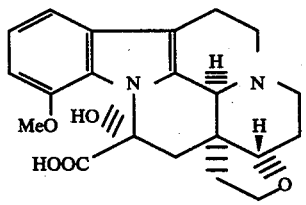

X is referred to as nor-cuanzine

EXAMPLE 1

21-Epicuanzine (A=β-H, B = CO$_2$Me, C=OH, D=H) hydrochloride 5 g of cuanzine were dissolved in 100 ml of acetic acid and treated with a solution containing 12.5 g of K$_2$Cr$_2$O$_7$ in 100 ml of water and 100 ml of acetic acid. After 24 hours, the mixture was diluted with 500 ml of a saturated aqueous solution of KClO$_4$ and left to crystallize. The solid obtained was filtered, dissolved in methanol and hydrogenated for 24 hours in the presence of carbon palladate. The solution was filtered from the catalyst, concentrated, made alkaline with dilute ammonia and extracted with chloroform.

The organic phase was then concentrated to dryness and the residue re-dissolved in methanol and treated with ether saturated with hydrochloric acid. 3.5 g of 21-epicuanzine hydrochloride were obtained; m.p. 114° C.

Found: C, 59.67; H, 6.29; N, 6.39; Cl, 8.09. Calculated: C, 60.76; H, 6.21; N, 6.44; Cl, 8.17 (for C$_{22}$H$_{27}$N$_2$O$_5$Cl).

EXAMPLE 2

Apocuanzine (A=α-H, B = CO$_2$Me, C and D =\_/)

A solution of 5 g of cuanzine in 350 ml of methanol containing 30 per cent of gaseous hydrochloric acid was heated to 60° C for one hour. The solution was then concentrated under vacuum to a small volume, diluted with water and made alkaline with saturated aqueous solution of sodium carbonate. Extraction was then carried out with ethyl acetate and the organic phase concentrated to a small volume and acidified with a methanol solution of tartaric acid. Apocuanzine tartrate (5 g) was filtered after 12 hours; m.p. 244° C Found: C, 58.74; H, 5.69; N, 5.31. Calculated: C, 58.87; H, 5.66; N, 5.28 (for C$_{26}$H$_{31}$N$_2$O$_{10}$)

EXAMPLE 3

N,N-dimethylaminoethyl nor-cuanzinate (A=α-H, B=CO$_2$CH$_2$CH$_2$NMe$_2$ C=OH, D=H dihydrochloride)

3.98 g of cuanzine were dissolved in 100 ml of ethanol and extracted for two hours under reflux in a nitrogen atmosphere with an aqueous solution (50 ml) containing 1.6 g of sodium hydroxide. Concentration under vacuum was carried out until a volume of 50 ml had been obtained. The concentrate was then neutralized with aqueous acetic acid and extracted three times with a mixture of n-butyl alcohol and benzene in a ratio of 4:1. The organic phase was evaporated to dryness, redissolved in 100 ml of isopropyl alcohol and treated under reflux for 5 hours with 5.4 g of ClCH$_2$CH$_2$NMe$_2$ and 6.9 g of K$_2$CO$_3$. The solution was left to cool, filtered from the precipitate and the filtrate evaporated to dryness. The residue was taken up in methanol containing 5 per cent of gaseous hydrochloric acid. By adding small amounts of ethyl ether, the product (2.7 g) crystallized; m.p. 230° C (dec.).

Found: C, 56.72; H, 6.57; N, 7.87; Cl, 13.53. Calculated: C, 56.82; H, 6.63; N, 7.95; Cl, 13.45 (for C$_{25}$H$_{35}$N$_3$Cl$_2$O$_5$).

EXAMPLE 4

Hydrazine derivatives of cuanzine (A=α-H; R$_3$=H,H; R$_4$=H,H.)

5 g of cuanzine were dissolved in 100 ml of ethanol and treated for two hours under heat with 100 ml of hydrazine hydrate. The mixture was then diluted with water and extracted with chloroform.

The organic phase was washed three times with water, dried over sodium sulphate, evaporated to dryness and the residue crystallized from methanol to give 4.6 g of a hydrazide, m.p. 209° C, which was believed to have the following structure

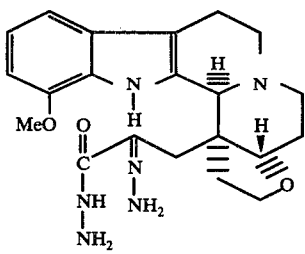

XI

Found: C, 61.10; H, 6.85; N, 20.37. Calculated: C, 61.16; H, 6.80; N, 20.39 (for $C_{21}H_{28}N_6O_3$).

EXAMPLE 5

Formation of Hydrazone from the Product of Example 4

3 g of product of Example 4 (XI) were dissolved in 30 ml of acetone and treated for 1 hour under reflux. After 24 hours at 10° C were crystallized 2.7 g of hydrazone. m.p. 185° C ms 452 (M+)

Found: C, 63.69; H, 7.10; N, 18.53. Calculated: C, 63.72; H, 7.08; N, 18.58 (for $C_{24}H_{32}N_6O_3$).

The following experimental data demonstrate the pharmaceutical properties of the compounds of the invention.

1. HAEMODYNAMIC ACTIVITIES IN ANAESTHETIZED DOGS

The products under investigation were administered intravenously to anaesthetized mongrel dogs in doses which were in proportion to the lethal dose (one twentieth of the $LD_{50}$).

The average of the carotid and femoral arterial pressures, the coronary and carotid and femoral arterial pressures, the coronary and femoral flow rates and the contractive power of the heart were measured and the results are shown in Table I.

All the new derivatives can be seen to be more active or, as in the case of the dimethylaminoethyl ester of cuanzine, as active as cuanzine.

2. SPASMOLYTIC ACTIVITY ON THE ISOLATED ILEUM OF GUINEA PIGS

Table 2 shows the results obtained in the study of the spasmolytic activity on the spasms produced by acetylcholine in the ileum of guinea pigs.

Table 1

| | | Haemodynamic activities in anaesthetized dogs | | | |
|---|---|---|---|---|---|
| | | Arterial pressure Average variation | | Flow | Contractive power of |
| Substances and doses mg/kg intravenously | | in mm Hg carotid femoral | | coronary (1) femoral (1) | heart (1) |
| Cuanzine hydrochloride | 8 | −10 | −10 | ++ + | = |
| Cuanzine hydrazide bitartrate | 10 | −30 | −30 | +++ ++ | + |
| 21-epicuanzine hydrochloride | 5 | −20 | −20 | ++ + | = |
| Apocuanzine hydrochloride | 2.5 | −15 | −15 | +++ + | + |
| Cuanzine dimethylaminoethyl ester dihydrochloride | 10 | −10 | −10 | ++ + | = |

(1) +++: intense increase
++: moderate increase
+: faint increase
=: no change

Table 2

| Substances (1) | Spasmolytic activity on the isolated ileum of guinea pigs |
|---|---|
| | $ED_{50}$ (γ/ml) and base limits on spasm (1) induced by 100 mg/ml of acetylcholine |
| Cuanzine hydrochloride | 120 (169.2 − 85.1) |
| Cuanzine hydrazide bitartrate | 74 (116.2 − 47.1) |
| 21-epicuanzine | 37 (68.8 − 19.9) |
| Apocuanzine | 26.5 (46.9 − 15) |

(1) The time of contact of the spasmogenic and spasmolytic substances was 1 and 3 minutes, respectively.
The interval between the administrations was 5 minutes.

PHARMACEUTICAL PREPARATION

The following examples illustrate the manner in which the compounds of the invention may be brought into forms suitable for oral and parenteral administration.

| Ampoules | |
|---|---|
| 1) 21-epicuanzine hydrochloride | 10 mg |
| Excipients (propylene glycol, water for injections) | up to 2 ml |
| 2) Apocuanzine | 10 mg |
| Excipients (propylene glycol, citric acid, water for injections) | up to 2 ml |

| Drops | |
|---|---|
| 1) N,N-dimethylaminoethyl nor-cuanzinate dihydrochloride | 200 mg |
| Excipients (ethyl alcohol, propylene glycol, purified water) | up to 10 ml |
| 2) 21-epicuanzine | 150 mg |
| Excipients (ethyl alcohol, propylene glycol, purified water) | up to 10 ml |

| Tablets | |
|---|---|
| 1) N,N-dimethylaminoethyl nor-cuanzinate | 20 mg |
| Excipients (starch, lactose, magnesium stearate, talc, arabic gum) | up to 200 mg |
| 2) Hydrazine derivative of cuanzine | 20 mg |
| Excipients (starch, lactose, magnesium stearate, talc, arabic gum) | up to 200 mg |

| Sugar coated tablets | |
|---|---|
| Product of Example 5 | 20 mg |
| Excipients (starch, lactose, magnesium stearate, talc, arabic gum, colophony, titanium bioxide, magnesium carbonate, saccarose) | up to 250 mg |

We claim:

1. A compound having the general formula

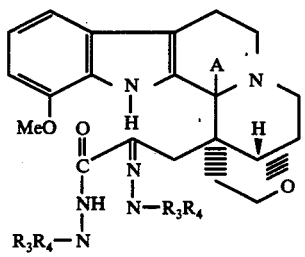

III wherein
A represents a hydrogen atom in the α- or β-configuration and
$R_3$ and $R_4$, which may be the same or different each represents a hydrogen atom or a $C_{1-6}$ alkyl group.

2. A hydrazone of a compound of formula III as claimed in claim 1 and having the structure

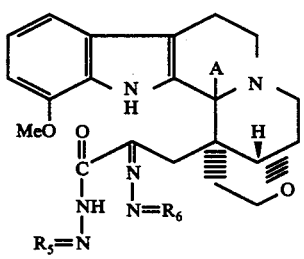

IV wherein A is defined in claim 1 and $R_5$ and $R_6$ are different and each represents two hydrogen atoms or a group $=CR_7R_8$ where $R_7$ and $R_8$, which may be the same or different each represents a $C_{1-6}$ alkyl group, a $C_{6-12}$ aryl group or a hydrogen atom.

3. A derivative of cuanzine obtainable by reacting cuanzine with hydrazine or a hydrazine derivative of formula $H_2NNR_3R_4$, wherein $R_3$ and $R_4$, which may be the same or different each represent a hydrogen atom or a $C_{1-6}$ alkyl group.

4. A monohydrazone obtainable by reacting a compound as claimed in claim 3 with an aldehyde or ketone of formula $R_7R_8CO$ wherein $R_7$ and $R_8$, which may be the same or different, each represent a $C_{1-6}$ alkyl group, a $C_{6-12}$ aryl group or a hydrogen atom.

5. A pharmaceutical composition having vasodilatory and hypotensive activity comprising a vasodilatory or hypotensive effective amount of a compound as claimed in claim 1 and a pharmaceutically acceptable diluent or carrier.

6. A composition according to claim 5 wherein A represents α-H and each of $R_3$ and $R_4$ represents H.

7. A pharmaceutical composition having vasodilatory and hypotensive activity comprising a vasodilatory or hypotensive effective amount of a cuanzine derivative as claimed in claim 2 and a pharmaceutically acceptable diluent or carrier.

8. A composition according to claim 7 wherein in formula IV, A represents α-H, one of $R_5$ and $R_6$ represents two hydrogen atoms and the other represents $=C(CH_3)_2$.

9. A pharmaceutical composition having vasodilatory and hypotensive activity comprising a vasodilatory or hypotensive effective amount of a compound as claimed in claim 3 and a pharmaceutically acceptable diluent or carrier.

10. A pharmaceutical composition having vasodilatory and hypotensive activity comprising a vasodilatory or hypotensive effective amount of a compound as claimed in claim 4 and a pharmaceutically acceptable diluent or carrier.

11. A method of treating patients in need of drugs with vasodilatory or hypotensive activity comprising orally or parenterally administering a vasodilatory or hypotensive dose of the composition in accordance with claim 5.

* * * * *